(12) United States Patent
Koppel et al.

(10) Patent No.: US 7,833,998 B2
(45) Date of Patent: Nov. 16, 2010

(54) ORAL NEUROTHERAPEUTIC CEPHALOSPORIN SULFOXIDE AND SULFONE-CONTAINING COMPOSITIONS

(75) Inventors: Gary A. Koppel, Indianapolis, IN (US); Michael O. Chaney, Carmel, IN (US)

(73) Assignee: Revaax Pharmaceuticals, LLC, Indianapolis, IN (US)

( * ) Notice: Subject to any disclaimer, the term of this patent is extended or adjusted under 35 U.S.C. 154(b) by 761 days.

(21) Appl. No.: 10/569,118

(22) PCT Filed: Aug. 24, 2004

(86) PCT No.: PCT/US2004/027451

§ 371 (c)(1),
(2), (4) Date: Feb. 22, 2006

(87) PCT Pub. No.: WO2005/020904

PCT Pub. Date: Mar. 10, 2005

(65) Prior Publication Data

US 2008/0176825 A1    Jul. 24, 2008

Related U.S. Application Data

(60) Provisional application No. 60/497,588, filed on Aug. 25, 2003, provisional application No. 60/533,132, filed on Dec. 30, 2003.

(51) Int. Cl.
C07D 501/36    (2006.01)
A61K 31/546    (2006.01)
A61P 25/24     (2006.01)
A61P 25/22     (2006.01)

(52) U.S. Cl. ........................... 514/206; 540/227
(58) Field of Classification Search ................ 540/227; 514/206
See application file for complete search history.

(56) References Cited

U.S. PATENT DOCUMENTS

| | | | | |
|---|---|---|---|---|
| 3,275,626 | A | | 9/1966 | Morin et al. |
| 4,138,555 | A | * | 2/1979 | Cook et al. ............... 540/222 |
| 4,237,128 | A | * | 12/1980 | Cimarusti et al. .......... 514/207 |
| 4,275,062 | A | * | 6/1981 | Breuer et al. ............. 514/206 |
| 4,349,672 | A | * | 9/1982 | Montavon et al. .......... 540/227 |
| 4,399,131 | A | * | 8/1983 | Durckheimer et al. ....... 514/201 |
| 4,547,371 | A | * | 10/1985 | Doherty et al. ............ 514/200 |
| 4,992,431 | A | * | 2/1991 | Heymes et al. ............ 514/202 |
| 5,077,286 | A | * | 12/1991 | Bissolino et al. .......... 514/201 |
| 5,147,871 | A | * | 9/1992 | Albrecht et al. ........... 514/202 |
| 5,258,377 | A | * | 11/1993 | Maiti et al. .............. 514/201 |
| 5,264,429 | A | * | 11/1993 | Maiti et al. .............. 514/202 |
| 5,264,430 | A | * | 11/1993 | Maiti et al. .............. 514/206 |
| 5,364,848 | A | * | 11/1994 | Doherty et al. ............ 514/201 |
| 5,439,904 | A | * | 8/1995 | Maiti et al. .............. 514/200 |
| 5,442,058 | A | | 8/1995 | Nieuwenhuis |
| 5,446,037 | A | * | 8/1995 | Maiti et al. .............. 514/201 |
| 5,580,865 | A | * | 12/1996 | Alpegiani et al. .......... 514/202 |
| 5,760,027 | A | * | 6/1998 | Buynak et al. ............ 514/200 |
| 6,489,319 | B2 | * | 12/2002 | Koppel et al. .......... 514/210.08 |
| 6,495,539 | B1 | * | 12/2002 | Hultgren et al. .......... 514/192 |
| 6,627,625 | B1 | * | 9/2003 | Koppel .................. 514/198 |
| 6,916,801 | B2 | * | 7/2005 | Buynak et al. ............ 514/200 |
| 7,112,582 | B2 | * | 9/2006 | Venkatesan et al. ........ 514/193 |
| 7,384,928 | B2 | * | 6/2008 | Nishitani et al. .......... 514/202 |
| 2002/0142950 | A1 | * | 10/2002 | Hayward et al. ........... 514/12 |
| 2003/0003526 | A1 | * | 1/2003 | Tsien et al. .............. 435/32 |
| 2007/0249523 | A1 | * | 10/2007 | Koppel et al. ............. 514/8 |
| 2008/0009634 | A1 | * | 1/2008 | Winkley et al. ........... 548/178 |

FOREIGN PATENT DOCUMENTS

| | | |
|---|---|---|
| CA | 1031768 | 5/1978 |
| DE | 635104 | 3/1983 |
| DE | 635105 | 3/1983 |

OTHER PUBLICATIONS

Wendel, Anesthesiology. 96(4):913-920, Apr. 2002.*
Richter, Wolfgang F.; Chong, Yong H.; Stella, Valentino J.; "On the Mechanism of Isomerization of Cephalosporin Esters", Journal of Pharmaceutical Sciences, vol. 79, No. 2, Feb. 1990, pp. 185-186.
Vorona, Maxim.; Veinberg, G.; Shestakova, I.; Kanepe, I.; Lukevics, E.; "Anticancer Activity in Vitro of Some Amides and Esters of 7α Chlorodeacetoxycephalosporanate Sulfone", RTU zinatniskie raksti, Materialzinatne un lietiska kimija 5, Sejuns 2002.g. pp. 190-194.
Adams, D.B. "Brain Mechanisms for Offense, Defense and Submission," *The Behavioral Brain Sciences* 2:201-241 (1979).
Albert, D.J. and Walsh, M.L., "Neural systems and the inhibitory modulation of agonistic behavior: a comparison of mammalian species," *Neurosci Biobehav Rev* 8(1):5-24 (1984).
Baumann MH, et al., "Effects of Phentermine and Fenfluramine on Extracellular Dopamine and Serotonin in Rat Nucleus Accumbens: Therapeutic Implications," Synapse 36(2):102-113 (2000).
Blanchard, D.C. (1984) *Applicability of animal models to human aggression* In: Biological Perspectives on Aggression, Alan R. Liss, Inc., pp. 49-74.
Blanchard, R.J., Blanchard, D.C., "Aggressive behavior in the rat," *Physiology and Behavior* 1:197-224 (1977).
Cartmell, J et al., "Dopamine and 5-HT turnover are increased by the mGlu2/3 receptor agonist LY379268 in rat medial prefrontal cortex, nucleus accumbens and striatum," Brain Research 887(2):378-384 (2000).
Cartmell, J. et al.. "The potent, selective mGlu2/3 receptor agonist LY379268 increases extracellular levels of dopamine, 3,4-dihydroxyphenylacetic acid, homovanillic acid, and 5-hydroxyindole-3-acetic acid in the medial prefrontal cortex of the freely moving rat," J Neurochemistry 75(3):1147-1154 (2000).
Charney, DS, and Bremner, JD (1999) The neurobiology of anxiety disorder. In: Neurobiology of Mental Illness (Charney, DS, et al eds.), Oxford University Press, New York, pp. 494-517.

(Continued)

*Primary Examiner*—Mark L Berch
(74) *Attorney, Agent, or Firm*—Venable LLP; Michael A. Gollin; Keith G. Haddaway

(57) ABSTRACT

The treatment of neurological disorders using cephalosporin sulfoxide-containing and/or cephalosporin sulfone-containing compositions and pharmaceutical compositions including oral dosage forms that include cephalosporin sulfoxide and/or sulfone-containing compositions are described.

10 Claims, 5 Drawing Sheets

OTHER PUBLICATIONS

Coccaro, EF et al., "Cerebrospinal Fluid Vasopressin Levels: Correlates With Aggression and Serotonin Function in Personality-Disordered Subjects," Arch Gen Psychiatry 55(8):708-14 (1998).

Crusio, WE et al., "Radial-Maze Performance and Structural Variation of the Hippocampus in Mice: A Correlation With Mossy Fibre Distribution," Brain Research 425(1):182-5 (1987).

Feighner JP, "Overview of Antidepressants Currently Used to Treat Anxiety Disorders," J Clin Psychiatry 60:18-22 (1999).

Ferris, C.F., & Potegal, M., "Vasopressin receptor blockade in the anterior hypothalamus suppresses aggression in hamsters," *Physiology and Behavior* 44:235-239 (1988).

Ferris, C.F., et al., "Scent marking and the maintenance of dominant/subordinate status in male golden hamsters," Physiology and Behavior 40:661-664 (1987).

Ferris, C.F., et al., "Vasopressin/Serotonin Interactions in the Anterior Hypothalamus Affect Aggressive Behavior in Golden Hamsters," J Neuroscience 17:4331-4340 (1997).

Hertel P, et al., "Risperidone: regional effects in vivo on release and metabolism of dopamine and serotonin in the rat brain," Psychopharmacology (Berl) 124(1-2):74-86 (1996).

Johnston, R.E. (1985) Communication, In: The Hamster Reproduction and Behavior. Ed Siegel, H.I. Plenum Press, New York, pp. 121-154.

King, JA et al., Seed Finding in Golden Hamsters: A Potential Animal Model for Screening Anxiolytic Drugs, *Neuropsychobiology* 45:150-155 (2002).

McKinney, W.T. (1989) *Basis of development of animal models in psychiatry: An overview.* In: Animal Models of Depression, Eds. G.G. Koob, C.L. Ehlers, E.J. Kupfer Birkanser, Boston.

Olton, D.S., & Samuelson, R.J., "Remembrance of Places Passed—Spatial Memory in Rats," J Exp Psychol Anim Behav Processes 2(2):97-116 (1976).

Pellow, S et al., "Validation of Open :Closed Arm Entries in an Elevated Plus-Maze As a Measure of Anxiety in the Rat," *Journal of Neuroscience Methods* 14(3):149-167 (1985).

Rothman, RB et al., "Hypothesis that mesolimbic dopamine (DA) plays a key role in mediating the reinforcing effects of drugs of abuse as well as the rewarding effects of ingestive behaviors," J Subst Abuse Treat 11:273-275 (1994).

Weintraub, M, et al., "A Double-Blind Clinical Trial in Weight Control. Use of Fenfluramine and Phentermine Alone and in Combination," Arch Intern Med 144(6):1143-8 (1984).

Batueva, I.V., Veselkin, N.P., Veskov, R., "Effect of Penicillin on the Synaptic Activity of Isolated Spinal Cord Motor Neurons in the Lamprey," Neirofiziologiia, vol. 24, No. 2, 1992, English Abstract, 2 pages.

Bashir, Z.I., Holmes, O., "N-methyl-D-aspartate Receptors and the Enhancement of Somatosensory Evoked Potentials in Penicillin Epileptogenesis in Rats," Physiological Society, Mar. 1987, 1 page.

Horn, E., Esseling, K., Wagner, R., "Time Course of Interictal EEG Patterns Induced by a Penicillin Injection Into the Olfactory Cortex," Pharmacology Biochemistry & Behavior, vol. 40, 1991, pp. 351-357.

Home, A.L., Hadingham, K.L., Macaulay, A.J., Whiting, P., Kemp, J.A., "The Pharmacology of Recombinant $GABA_A$ Receptors Containing Bovine $\alpha_1$, $\beta_1$, $\gamma_{2L}$ Sub-Units Stably Transfected Into Mouse Fibroblast L-Cells," Br. J. Pharmacol. vol. 107, 1992, pp. 732-737.

Kalueff, A.V., Samonina, G.E., Ashmarin, I.P., "Penicillins and Their Derivatives: Antiulcer/Antistress Properties?," Neuropsychoharmacology, vol. 10, No. 36, Part 2, 1994, 1 page.

Orwar, O., Li, X., Andine, P., Bergstrom, C.M., Hagberg, H., Folestad, S., Sandberg, M., "Increased Intra- and Extracellular Concentrations of γ-Glutamylglutamate and Related Dipeptides in the Ischemic Rat Striatum: Involvement of γ-Glutamyl Transpeptidase," Journal of Neurochemistry, vol. 63, 1994, pp. 1371-1376.

Serval, V., Barbeito, L., Pittaluga, A., Cheramy, A., Lavielle, S., Glowinski, J., "Competitive Inhibition of N-Acetylated-α-Linked Acidic Dipeptidase Activity by N-Acetyl-L-Aspartyl-β-Linked L-Glutamate," Journal of Neurochemistry, vol. 55, 1990, pp. 39-46.

Varga, V., Janaky, R., Saransaari, P., Oja, S.S., "Endogenous γ-L-Glutamyl and β-L-Aspartyl Peptides and Excitatory Aminoacidergic Neurotransmission in the Brain," Neuropeptides, vol. 27, 1994, pp. 19-26.

\* cited by examiner

ORAL NEUROTHERAPEUTIC CEPHALOSPORIN SULFOXIDE AND SULFONE-CONTAINING COMPOSITIONS

CROSS-REFERENCE TO RELATED APPLICATIONS

This application is a U.S. national application under 37 C.F.R. §371(b) of International Application Serial No. PCT/US2004/027451 filed Aug. 24, 2004, which claims the benefit, under 35 U.S.C. §119(e), of U.S. Provisional Patent Application Ser. Nos. 60/497,588 and 60/533,132 filed Aug. 25, 2003, and Dec. 30, 2003, respectively.

FIELD OF INVENTION

This invention relates to compounds and methods for neuropsychiatric intervention. More particularly, this invention is directed to pharmaceutical formulations and methods for treatment of a variety of neurological disease states using cephalosporin sulfoxides, cephalosporin sulfones, their pharmaceutically acceptable salts, and their active esters, illustratively in oral dosage form.

BACKGROUND AND SUMMARY OF THE INVENTION

The pharmaceutical industry has directed extensive research and development efforts toward discovery and commercialization of drugs for treatment of neurological disorders. Such disorders typically derive from chemical imbalances in the brain. Overproduction or underproduction of pertinent neurochemical species and/or receptor dysfunction has been identified with many disease states recognized by neurologists, psychiatrists, psychologists and other medical practitioners skilled in the diagnosis and treatment of mental disease. Most of the discovery efforts for new neurologically active drugs have been based on the study of agonist/antagonist drug interactions with one or more of the numerous receptors in the brain and/or their respective receptor ligands.

The present invention provides for the use of oral dosage forms of cefazolin compounds and derivatives thereof as psychotherapeutics in the treatment of various neurological disorders.

BRIEF DESCRIPTION OF THE DRAWINGS

FIG. 2*a* shows latency to enter the closed arm, while FIG. 2*b* shows time in the open arm.

FIG. 3*a* shows latency to bite, FIG. 3*b* shows contact time, FIG. 3*c* shows number of bites, and FIG. 3*d* shows number of flank marks.

DETAILED DESCRIPTION OF THE INVENTION

Figures 1A, 1B:
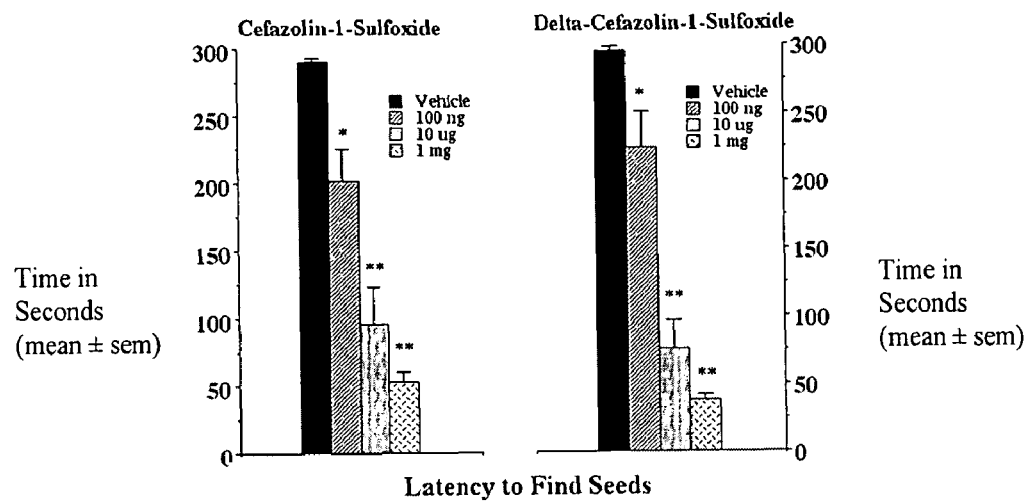
FIGS. 1*a-b* show results using $\Delta^3$-cefazolin-1-sulfoxide (FIG. 1*a*) and $\Delta^2$-cefazolin-1-sulfoxide (FIG. 1*b*) in a dose-response study in the seed finding model of anxiety.

The present invention and the various embodiments described and claimed herein derive, in part, from the discovery that certain carboxypeptidase E inhibitors exhibit potent neurotherapeutic activity when administered to provide effective threshold enzyme inhibitory concentrations of the same in the brain. Such inhibitors exhibit clinically significant neuroactivity evidenced in part by behavioral modification and enhanced cognition. Based on currently available test data and molecular modeling studies, it is now suggested that neurogenic carboxypeptidase E can be targeted/inhibited to provide basis for a multiplicity of neurotherapeutic effects. Carboxypeptidase E binding site models have identified certain cephalosporin sulfoxides and sulfones, illustratively $\Delta^2$- and $\Delta^3$-cefazolin sulfoxides as potential inhibitors of carboxypeptidase E. While cefazolin itself has some serenic activity, both $\Delta^2$- and $\Delta^3$-cefazolin sulfoxides have demonstrated both serenic and anxiolytic activity. Moreover, while cefazolin is known to have some antibiotic activity when administered parenterally, the cephalosporin sulfoxides and sulfones of the present invention have demonstrated both serenic and anxiolytic activity in hamsters, even when administered orally. Thus, one embodiment of this invention is the use of $\Delta^2$- and $\Delta^3$-cefazolin sulfoxides and sulfones and derivatives thereof (see Formula II below) as psychotherapeutics in the treatment of aggression, obsessive-compulsive disorder, anxiety, cognitive disorders, and the like. In one particular embodiment, the $\Delta^2$- and $\Delta^3$-cefazolin sulfoxides and derivatives thereof are provided in oral dosage forms.

Exemplary of behavioral and cognitive disorders susceptible to treatment in accordance with this invention include aggressive disorder, obsessive-compulsive disorder, anxiety, depression, schizophrenia, ADHD, and diseases evidenced by memory/learning impairment. Preliminary animal data indicate that the methods and compositions of this invention may be used in the treatment of neurotherapeutic disorders as anti-aggressive agents to control impulsivity and violence, illustratively in autism, Tourette's syndrome, mental retardation, psychosis, mania, senile dementia, and in the treatment of individuals with personality disorders and history of inappropriate aggression. Clinical applications extend as well, for example, to the treatment of children with ADHD and conduct disorder, as an anxiolytic, as a cognition enhancer for the geriatric population to improve learning and memory and to ameliorate disorientation. In accordance with this invention the cephalosporin sulfoxides and sulfones, illustratively oral dosage forms of $\Delta^2$- and $\Delta^3$-cefazolin sulfoxides and derivatives thereof, can be used in a multiplicity of psychotherapeutic applications.

The neurothoerapeutic cephalosporin compounds for use in preparing the oral dosage forms of this invention are generally compounds of the formulae

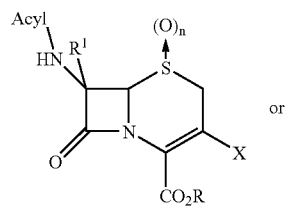

Formula Ia or

-continued

Formula Ib

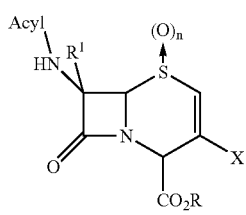

wherein n is 1 or 2;

R is hydrogen, an active ester forming group, or a pharmaceutically acceptable cation;

$R^1$ is hydrogen; optionally substituted alkyl, including lower alkyl and $C_1$-$C_4$ alkyl, such as methyl, ethyl, propyl, and the like; optionally substituted alkoxy, including lower alkoxy and the group ($C_1$-$C_4$ alkyl)-O—, or optionally substituted alkylthio, such as lower alkylthio and the group ($C_1$-$C_4$ alkyl)-S—, including methylthio and ethylthio;

Acyl is a residue of a carboxylic acid, such as $R^2$—$CO_2H$, where $R^2$ is alkyl, aryl, arylalkyl, heteroaryl, or heteroarylalkyl, each of which may be optionally substituted; and X is hydrogen, alkyl, including lower alkyl and $C_1$-$C_6$ alkyl, halo, haloalkyl, hydroxy, alkoxyalkyl, haloalkoxyalkyl, alkoxyalkoxy, alkylthio, optionally substituted arylthio, optionally substituted heteroarylthio, acyloxy, wherein acyl is as described above, such as optionally substituted alkylcarbonyloxy, optionally substituted arylcarbonyloxy, and optionally substituted heteroarylcarbonyloxy; or X is —$CH_2B$, wherein B is the residue of a nucleophile B—H.

Illustratively, Acyl is a radical, attached at the (*) atom, having one of the following structures:

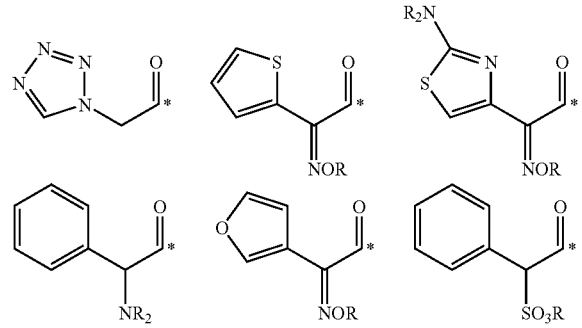

wherein R is in each occurrence independently selected from hydrogen, optionally substituted alkyl, and pharmaceutically acceptable cations; and each aryl or heteroaryl that forms part of Acyl as described herein is optionally substituted.

The nucleophile B—H is any nucleophile capable of displacing a leaving group (L) on a molecule, such as a compound having the formula:

Formula Ic

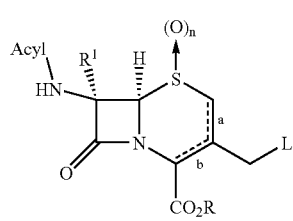

or a protected derivative thereof, wherein n is 1 or 2;

R is hydrogen, an active ester forming group, or a pharmaceutically acceptable cation;

R1 is hydrogen, alkyl, alkoxy, or alkylthio;

Acyl is as defined for compounds of Formulae Ia and Ib; and

L is a leaving group, such as halo, alkoxy, aryloxy, alkylcarbonyloxy, haloalkylcarbonyloxy, arylcarbonyloxy, alkylsulfonyloxy, haloalkylsufonyloxy, and the like, and substituted derivatives thereof.

Illustratively, X is —$CH2B$, where B is a radical, attached at the (*) atom, having one of the following structures:

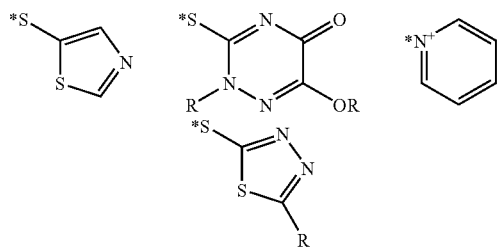

wherein R is in each occurrence independently selected from hydrogen, optionally substituted alkyl, and pharmaceutically acceptable cations; and each heteroaryl that forms part of X as described herein is optionally substituted.

Illustratively, the neurotherapeutic cephalosporin compounds are cefazolin derivatives and have the formula:

Formula II

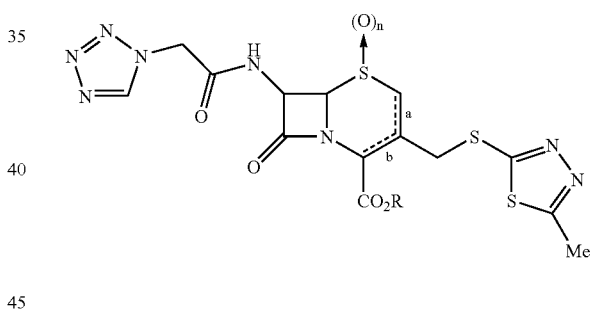

wherein n is 1 or 2;

one of bond a or bond b is a double bond; and

R is hydrogen, an active ester forming group, or a pharmaceutically acceptable cation.

More illustratively, the neurotherapeutic compounds have the following structures, wherein Formula III is $\Delta^2$-cefazolin sulfoxide (or delta-2-cefazolin-1-sulfoxide), and Formula IV is $\Delta^3$-cefazolin sulfoxide (or cefazolin-1-sulfoxide).

Formula III

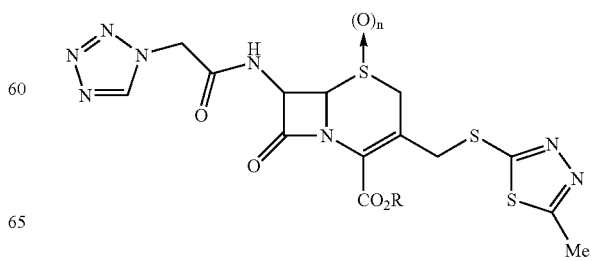

Formula IV

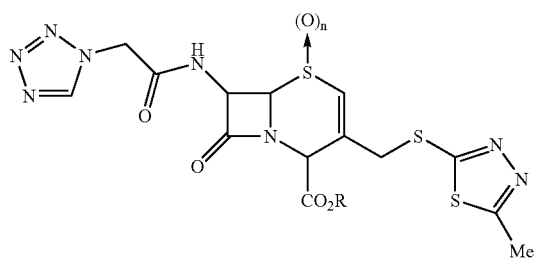

wherein n is 1 or 2, and R is hydrogen or a pharmaceutically acceptable cation.

The present invention is also directed to a pharmaceutical composition comprising a compound selected from those described above, and a pharmaceutically acceptable carrier, diluent, or excipient.

The general chemical terms used in the formulae above have their usual meanings. For example, the term "alkyl" includes such groups as methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like.

The term "aryl" refers to an aromatic ring or heteroaromatic ring and includes such groups as furyl, pyrrolyl, thienyl, thiazolyl, oxazolyl, isoxazolyl, isothiazolyl, imidazolyl, pyrazolyl, tetrazolyl, phenyl, pyridinyl, pyridazinyl, pyrimidinyl, pyrazinyl, thiadiazolyl, oxadiazolyl, naphthyl, indanyl, fluorenyl, quinolinyl, isoquinolinyl, benzodioxanyl, benzofuranyl, benzothienyl, and the like.

The term "optionally-substituted" refers to the replacement of one or more, preferably from one to three, hydrogen atoms with one or more substitutents. Such substituents include such groups as $C_1$-$C_4$ alkyl, $C_1$-$C_4$ alkoxy, $C_1$-$C_4$ alkylthio, hydroxy, nitro, halo, carboxy, cyano, $C_1$-$C_4$ haloalkyl, $C_1$-$C_4$ haloalkoxy, $C_1$-$C_4$ alkoxyalkyl, $C_1$-$C_4$ haloalkoxyalkyl, amino, carboxamido, amino, mono($C_1$-$C_4$ alkyl)amino, di($C_1$-$C_4$ alkyl)amino, $C_1$-$C_4$ alkylsulfonyl, $C_1$-$C_4$ alkylsulfonylamino, and the like.

The terms "acyl" and "alkanoyl" include such groups as formyl, acetyl, propanoyl, butanoyl, pentanoyl, and the like.

The term "halo" means fluoro, chloro, bromo, and iodo.

It is understood that the terms described herein may be combined in chemically relevant ways. For example, the term "arylalkyl" refers to an optionally substituted aromatic ring or heteroaromatic ring linked to an alkyl chain, including but not limited to benzyl, tolyl, 2-, 3-, and 4-picolinyl, pyrimidinylethyl, 2-(thien-2-yl)propyl, and the like.

The term "pharmaceutically acceptable cation" refers to the cationic residue of any pharmaceutically acceptable salt that is capable of combining with a neurotherapeutic compound described herein to form the corresponding carboxylic acid salt under appropriate reaction, solvent, pH, or buffering conditions. These cations may also be prepared by cation exchange in the conventional manner. It is understood that such salt derivatives of the neurotherapeutic compounds described herein include the isolated forms in addition to forms that are present in solution as a consequence of the reaction, solvent, pH, or buffering conditions.

Illustrative pharmaceutically acceptable cations include, but are not limited to inorganic cations, including aluminum, silver; alkali metal salts such as lithium, sodium, or potassium; alkaline earth metal salts such as calcium or magnesium, and ammonium and substituted ammonium salts, and the like. Illustrative pharmaceutically acceptable cations include, but are not limited to organic cations, including alkylammoniums such as triethylammonium, hydroxyalkylammoniums such as 2-hydroxyethylammonium, bis-(2-hydroxyethyl) ammonium, and tris-(2-hydroxyethyl) ammonium, cycloalkylammoniums such as pyrrolidinium, piperidinium, dicyclohexylammonium, dibenzylammonium, N,N-dibenzylethylenediammonium, 1-ephenammonium, N-methylmorpholinium, ethylpiperidinium, N-benzyl-β-phenethylammonium, dehydroabietylammonium, N,N'-bis-dehydroabietylammonium, ethylenediammonium, pyridiniums such as pyridinium, collidinium, quinolinium, cetyl pyridinium, and tetradecylethyl pyridinium; and biguanidinium, and the like. Illustrative pharmaceutically acceptable cations include, but are not limited to mixed inorganic/organic cations, including copper glycinate, and the like.

The term "active ester forming group" refers to groups forming carboxylate derivatives that are hydrolyzed in vivo, under appropriately selected conditions, to the parent carboxylic acid. Such groups include prodrugs. Illustrative active ester forming groups include, but are not limited to, 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, and the like; dialkylaminoalkyl groups, such as ethoxycarbonyloxymethyl, β-ethoxycarbonyloxyethyl, and the like; dialkylaminoalkyl, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidy, dimethoxyphthalidyl, and the like.

The cephalosporin sulfoxides used in preparation of the illustrative oral dosage forms are prepared typically by oxidation of the corresponding art-recognized 2-cephem or 3-cephem compounds, for example using peracids, such as peracetic acid, m-chloroperbenzoic acid (mCPBA), and the like. The sulfones are prepared similarly by oxidation of the sulfoxide analogs or directly from the 2-cephem or 3-cephem analogs with excess oxidizing agent, such as the peracids described herein, hydrogen peroxide, and the like, illustratively in the presence of ruthenium tetroxide.

Based on animal tests to date, it is believed that the general classes of behavioral disorders that can be treated in accordance with this invention by administration of effective amounts of cephalosporin sulfoxides and sulfones, illustratively oral dosage forms of $\Delta^2$- and $\Delta^3$-cefazolin sulfoxides and derivatives thereof, include aggressive disorder, obsessive-compulsive disorder, anxiety, depression, and attention deficit hyperactivity disease (ADHD). Thus, in one embodiment of the invention a $\Delta^2$- or $\Delta^3$-cefazolin sulfoxide, or a combination of $\Delta^2$ and $\Delta^3$-cefazolin sulfoxides, is administered as an anti-aggressive agent to control impulsivity and violence in a patient afflicted with autism, Tourette's syndrome, mental retardation, psychosis, mania, senile dementia, or that in a patient with a personality disorder and history of inappropriate aggression.

Other neurological disease states which can be treated in accordance with the present invention include depression, including major depression (single episode, recurrent, melancholic), atypical, dysthmia, subsyndromal, agitated, retarded, co-morbid with cancer, diabetes, or post-myocardial infarction, involutional, bipolar disorder, psychotic depression, endogenous and reactive, obsessive-compulsive disorder, or bulimia. In addition, peptidase inhibitors can be used to treat patients suffering from pain (given alone or in combination with morphine, codeine, or dextropropoxyphene), obsessive-compulsive personality disorder, post-traumatic stress disorder, hypertension, atherosclerosis, anxiety, anorexia nervosa, panic, social phobia, stuttering, sleep disorders, chronic fatigue, cognition deficit associated with Alzheimer's disease, alcohol abuse, appetite disorders, weight loss, agoraphobia, improving memory, amnesia, smoking cessation, nicotine withdrawal syndrome symptoms, disturbances of mood and/or appetite associated with pre-menstrual syndrome, depressed mood and/or carbohydrate craving associated with pre-menstrual syndrome, disturbances of mood, disturbances of appetite or disturbances which contribute to recidivism associated with nicotine withdrawal, circadian rhythm disorder, borderline personality disorder, hypochondriasis, pre-menstrual syndrome (PMS), late luteal phase dysphoric disorder, premenstrual dysphoric disorder, trichotillomania, symptoms following discontinuation of other antidepressants, aggressive/intermittent explosive disorder, compulsive gambling, compulsive spending, compulsive sex, psychoactive substance use disorder, sexual disorder, schizophrenia, premature ejaculation, or psychiatric symptoms selected from stress, worry, anger, rejection sensitivity, and lack of mental or physical energy.

Other examples of pathologic, psychologic conditions which may be treated in accordance with this invention include, but are not limited to: Moderate Mental Retardation (318.00), Severe Mental Retardation (318.10), Profound Mental Retardation (318.20), Unspecified Mental Retardation (319.00), Autistic Disorder (299.00), Pervasive Development Disorder NOS (299.80), Attention-Deficit Hyperactivity Disorder (314.01), Conduct Disorder, Group Type (312.20), Conduct Disorder, Solitary Aggressive Type (312.00), Conduct Disorder, Undifferentiated Type (312.90), Tourette's Disorder (307.23), Chronic Motor or Vocal Tic Disorder (307.22), Transient Tic Disorder (307.21), Tic Disorder NOS (307.20), Primary Degenerative Dementia of the Alzheimer Type, Senile Onset, Uncomplicated (290.00), Primary Degenerative Dementia of The Alzheimer Type, Senile Onset, with Delirium (290.30), Primary Degenerative Dementia of the Alzheimer Type, Senile Onset, with Delusions (390.20), Primary Degenerative Dementia of the Alzheimer Type, Senile Onset, with Depression (290.21), Primary Degenerative Dementia of the Alzheimer Type, Presenile Onset, Uncomplicated (290.10), Primary Degenerative Dementia of the Alzheimer Type, Presenile Onset, with Delirium (290.11), Primary Degenerative Dementia of the Alzheimer Type, Presenile Onset, with Delusions (290.12), Primary Degenerative Dementia of the Alzheimer Type, Presenile Onset, with Depression (290.13), Multi-infarct dementia, Uncomplicated (290.40), Multi-infarct dementia, with Delirium (290.41), Multi-infarct Dementia, with Delusions (290.42), Multi-infarct Dementia, with Depression (290.43), Senile Dementia NOS (290.10), Presenile Dementia NOS (290.10), Alcohol Withdrawal Delirium (291.00), Alcohol Hallucinosis (291.30), Alcohol Dementia Associated with Alcoholism (291.20), Amphetamine or Similarly Acting Sympathomimetic Intoxication (305.70), Amphetamine or Similarly Acting Sympathomimetic Delusional Disorder (292.11), Cannabis Delusional Disorder (292.11), Cocaine Intoxication (305.60), Cocaine Delirium (292.81), Cocaine Delusional Disorder (292.11), Hallucinogen Hallucinosis (305.30), Hallucinogen Delusional Disorder (292.11), Hallucinogen Mood Disorder (292.84), Hallucinogen Posthallucinogen Perception Disorder (292.89), Phencyclidine (PCP or Similarly Acting Arylcyclohexylamine Intoxication (305.90), Phencyclidine (PCP) or Similarly Acting Arylcyclohexylamine Delirium (292.81), Phencyclidine (PCP) or Similarly Acting Arylcyclohexylamine Delusional Disorder (292.11), Phencyclidine (PCP) or Similarly Acting Arylcyclohexylamine Hood Disorder (292.84), Phencyclidine (PCP) or Similarly Acting Arylcyclohexylamine Organic Mental Disorder NOS (292.90), Other or unspecified Psychoactive Substance Intoxication (305.90), Other or Unspecified Psychoactive Substance Delirium (292.81), Other or Unspecified Psychoactive Substance Dementia (292.82), Other or Unspecified Psychoactive Substance Delusional Disorder (292.11), Other or Unspecified Psychoactive Substance Hallucinosis (292.12), Other or Unspecified Psychoactive Substance Mood Disorder (292.84), Other or Unspecified Psychoactive Substance Anxiety Disorder (292.89), Other or Unspecified Psychoactive Substance Personality Disorder (292.89), Other or Unspecified Psychoactive Substance Organic Mental Disorder NOS (292.90), Delirium (293.00), Dementia (294.10), Organic Delusional Disorder (293.81), Organic Hallucinosis (293.81), Organic Mood Disorder (293.83), Organic Anxiety Disorder (294.80), Organic Personality Disorder (310.10), Organic Mental Disorder (29.80), Obsessive Compulsive Disorder (300.30), Post-traumatic Stress Disorder (309.89), Generalized Anxiety Disorder (300.02), Anxiety Disorder NOS (300.00), Body Dysmorphic Disorder (300.70), Hypochondriasis (or Hypochondriacal Neurosis) (300.70), Somatization Disorder (300.81), Undifferentiated Somatoform Disorder (300.70), Somatoform Disorder NOS (300.70), Intermittent Explosive Disorder (312.34), Kleptomania (312.32), Pathological Gambling (312.31), Pyromania (312.33), Trichotillomania (312.39), and Impulse Control Disorder NOS (312.39).

Additional examples of pathologic psychological conditions which may be treated as described in this invention include: Schizophrenia, Catatonic, Subchronic, (295.21), Schizophrenia, Catatonic, Chronic (295.22), Schizophrenia, Catatonic, Subchronic with Acute Exacerbation (295.23), Schizophrenia, Catatonic, Chronic with Acute Exacerbation (295.24), Schizophrenia, Catatonic, in Remission (295.55), Schizophrenia, Catatonic, Unspecified (295.20), Schizophrenia, Disorganized, Chronic (295.12), Schizophrenia, Disorganized, Subchronic with Acute Exacerbation (295.13), Schizophrenia, Disorganized, Chronic with Acute Exacerbation (295.14), Schizophrenia, Disorganized, in Remission (295.15), Schizophrenia, Disorganized, Unspecified (295.10), Schizophrenia, Paranoid, Subchronic 295.31), Schizophrenia, Paranoid, Chronic (295.32), Schizophrenia, Paranoid, Subchronic with Acute Exacerbation (295.33), Schizophrenia, Paranoid, Chronic with Acute Exacerbation (295.34), Schizophrenia, Paranoid, in Remission (295.35), Schizophrenia, Paranoid, Unspecified (295.30), Schizophrenia, Undifferentiated, Subchronic (295.91), Schizophrenia, Undifferentiated, Chronic (295.92), Schizophrenia, Undifferentiated, Subchronic with Acute Exacerbation (295.93), Schizophrenia, Undifferentiated, Chronic with Acute Exacerbation (295.94), Schizophrenia, Undifferentiated, in Remission (295.95), Schizophrenia, Undifferentiated, Unspecified (295.90), Schizophrenia, Residual, Subchronic (295.61), Schizophrenia, Residual, Chronic (295.62), Schizophrenia, Residual, Subchronic with Acute Exacerbation (295.63), Schizophrenia, Residual, Chronic with Acute Exacerbation (295.94), Schizophrenia, Residual, in Remission (295.65), Schizophrenia, Residual, unspecified (295.60), Delusional (Paranoid) Disorder (297.10), Brief Reactive Psychosis (298.80), Schizophreniform Disorder (295.40), Schizoaffective Disorder (295.70), induced Psychotic Disorder (297.30), Psychotic Disorder NOS (Atypical Psychosis) (298.90), Bipolar Disorder, Mixed, Severe, without Psychotic Features (296.63), Bipolar Disorder, Manic, Severe, without Psychotic Features (296.43), Bipolar Disorder, Depressed, Severe, without Psychotic Features (296.53), Bipolar Disorder, Mixed, with Psychotic Features (296.64), Bipolar Disorder, Manic, with Psychotic Features (296.44), Bipolar Disorder, Depressed, with Psychotic Features (296.54), Bipolar Disorder NOS (296.70), Major Depression, Single Episode, with Psychotic Features (296.24), Major Depression, Recurrent with Psychotic Features (296.34) Personality Disorders, Paranoid (301.00), Personality Disorders, Schizoid (301.20), Personality Disorders, Schizotypal (301.22), Personality Disorders, Antisocial (301.70), and Personality Disorders, Borderline (301.83).

Anxiety disorders which may be treated in accordance with this invention include: Anxiety Disorders (235), Panic Disorder (235), Panic Disorder with Agoraphobia (300.21), Panic Disorder without Agoraphobia (300.01), Agoraphobia without History of Panic Disorders (300.22), Social Phobia (300.23), Simple Phobia (300.29), Organic Anxiety Disorder (294.80), Psychoactive Substance Anxiety Disorder (292.89), Separation Anxiety Disorder (309.21), Avoidant Disorder of Childhood or Adolescence (313.21), and Overanxious Disorder (313.00).

Effective amounts of the carboxypeptidase inhibiting compounds described herein, can be used for the treatment of the following pathologic psychological conditions: Moderate Mental Retardation; Severe Mental Retardation; Profound Mental Retardation; Autistic Disorder; Attention-Deficit Hyperactivity Disorder; Pervasive Development Disorder NOS; Conduct Disorder, Group Type; Conduct Disorder, Solitary Aggressive Type; Tourette's Disorder; Primary Degenerative Dementia of the Alzheimer Type, Senile Onset, with Delirium; Primary Degenerative Dementia of the Alzheimer Type, Senile Onset, with Delusions; Primary Degenerative Dementia of the Alzheimer Type, Presenile Onset; Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis); Bipolar Disorder, Mixed, with Psychotic Features; Bipolar Disorder, Manic, with Psychotic Features; Bipolar Disorder, Depressed, with Psychotic Features; Bipolar Disorder NOS; Major Depression, Single Episode, or Recurrent with Psychotic Features; Personality Disorders, Paranoid; Personality Disorders, Schizoid; Personality Disorders, Schizotypal; Personality Disorders, Antisocial; Personality Disorders, Borderline, Anxiety Disorders, Panic Disorder, Panic Disorder with Agoraphobia, Panic Disorder without Agoraphobia, Agoraphobia without History of Panic Disorders, Social Phobia, Simple Phobia, Obsessive Compulsive Disorder, Post-Traumatic Stress Disorder, Generalized Anxiety Disorder, Anxiety Disorder NOS, Organic Anxiety Disorder, Psychoactive Substance Anxiety Disorder, Separation Anxiety Disorder, Avoidant Disorder of Childhood or Adolescence, and Overanxious Disorder.

One or more of the present compounds can be used alone or in combination with P-glycoprotein inhibitors to treat the following psychotic conditions: Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis); Bipolar Disorder, Mixed, with Psychotic Features; Bipolar Disorder, Manic, with Psychotic Features; Bipolar Disorder, Depressed, with Psychotic Features; Bipolar Disorder NOS; Personality Disorders, Paranoid; Personality Disorders, Schizoid; Personality Disorders, Schizotypal; Personality Disorders, Antisocial; and Personality Disorders, Borderline.

Examples of psychotic conditions which are most preferably treated in accordance with the method of this invention include: Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Personality Disorders, Schizoid; and Personality Disorders, Schizotypal.

In one preferred aspect of this invention there is provided a treatment for anxiety. Examples of anxiety disorders which are treated using the present method and pharmaceutical formulations of this invention, include Anxiety Disorders, Panic Disorder, Panic Disorder with Agoraphobia, Panic Disorder without Agoraphobia, Agoraphobia without History of Panic Disorders, Social Phobia, Simple Phobia, Obsessive Compulsive Disorder, Post-Traumatic Stress Disorder, Generalized Anxiety Disorder, Anxiety Disorder NOS, Organic Anxiety Disorder, Psychoactive Substance Anxiety Disorder, Separation Anxiety Disorder, Avoidant Disorder of Childhood or Adolescence, and Overanxious Disorder.

Examples of the anxiety disorders which are most preferably treated include Panic Disorder; Social Phobia; Simple Phobia; Organic Anxiety Disorder; Obsessive Compulsive Disorder; Post-traumatic Stress Disorder; Generalized Anxiety Disorder; and Anxiety Disorder NOS.

It is understood that these lists are not inclusive and that other disorders may be treated with the compositions described herein.

The effective dose of the cephalosporin sulfoxides and sulfones and derivatives thereof when used in accordance with this invention will vary depending on several factors, including but not limited to their inherent affinity for the target peptidase, the selected route of administration, patient weight, blood-brain barrier transport efficiency, and the like. The effective doses of the cephalosporin sulfoxides and sulfones and derivatives thereof used in accordance with the present invention can be readily determined empirically using animal models coupled with the use of art-recognized analytical techniques. Illustratively, oral doses can range from about 2.5 ng/kg to about 30 mg/kg of body weight, representing doses of about 100 ng to about 1 g per dose. Higher or lower dosage amounts may be appropriate and used in accordance with this invention when patient circumstances dictate such in the judgment of the attending physician.

The present invention further provides for certain pharmaceutical formulations for the treatment of behavioral or cognitive disorders. Generally the formulation comprises one or more cephalosporin sulfoxides or sulfones of Formula I, more particularly one or more $\Delta^2$- or $\Delta^3$-cefazolin sulfoxides of Formula II, and a pharmaceutically acceptable carrier therefor. The amount of the compound is that amount effective to provide upon delivery by the predetermined route of administration, a concentration of the compound in the tissue the compound is desired, i.e., in the brain effective to treat and reduce symptoms of the targeted behavioral or cognitive disorders or other disorders that presumably can be treated by inhibition of carboxypeptidase E activity. The compounds used in accordance with this invention can be combined with one or more pharmaceutically acceptable carriers, and may be administered, for example, orally in such forms as tablets, capsules, caplets, dispersible powders, granules, lozenges, mucosal patches, sachets, and the like. The compound can be combined with a pharmaceutically acceptable carrier, for example starch, maltose, lactose, or trehalose, alone or in combination with one or more tableting excipients, and pressed into tablets or lozenges. Optionally, such tablets, caplets, or capsules can be enterically coated to minimize hydrolysis/degradation in the stomach. Oral dosage formulations contain from about 0.00001 to about 99% by weight active ingredient and about 1 to more than 99% by weight of one or more pharmaceutically acceptable carriers and/or formulating excipients. Optionally, the dosage forms can be formulated by combining the compound with, for example, a P-glycoprotein inhibitor to provide enhanced drug half-life and brain concentrations of the active ingredient. Alternatively, the compound can be simply co-administered with a P-glycoprotein inhibitor.

In another embodiment of the invention, pharmaceutical preparations may contain, for example, from about 4 µg to about 100 mg of the active ingredient in combination with the carrier, representing dosages from about 100 ng/kg to about 30 mg/kg of body weight. It is contemplated that as much as about 300 mg/kg of body weight can also be effective. The pharmaceutical formulation in accordance with one embodiment of this invention is formulated for per os (po) administration, i.e., oral ingestion administration or buccal or sublingual administration (in the form of sachets, lozenges, and/or mucosal patches). In another embodiment the dosage form is formulated for per os administration in a prolonged release dosage form formulated to release the active ingredient over a predetermined period of time.

While the illustrative embodiments include oral dosage forms, other dosage forms are possible. For example, topical dosage forms, including transdermal patches, intranasal, and suppository dosage unit formulations containing the cephalosporin sulfoxides and sulfones of this invention and conventional non-toxic pharmaceutically acceptable carriers, adjuvants, and vehicles adapted for such routes of administration, are also within the scope of this invention.

The pharmaceutical formulations in accordance with this invention alternatively can be delivered via parenteral routes of administration, including subcutaneous administration, intraperitoneal administration, intramuscular administration, and intravenous administration. Such parenteral dosage forms are typically in the form of aqueous solutions or dispersions using a pharmaceutically acceptable carrier such as isotonic saline, 5% glucose, or other well known pharmaceutically acceptable liquid carrier compositions.

The pharmaceutical forms suitable for injectable use include sterile aqueous solutions or dispersions and sterile powders or lyophilizates for the extemporaneous preparation of sterile injectable solutions or dispersions. The dosage forms are illustratively sterile and stable under the conditions of manufacture and storage, and preserved against the contaminating action of microorganisms. The carrier for injectable formulations can be a solvent or dispersion medium containing, for example, water, ethanol, or a polyol (or example glycerol, propylene glycol and liquid polyethylene glycol), mixtures thereof, and vegetable oil.

Parenteral dosage forms of the cephalosporin sulfoxides and sulfones useful for treatment of behavioral and cognitive disorders and other disease states responsive to neurogenic peptidase inhibition can also be formulated as injectable prolonged release formulations in which the active compound is combined with one or more natural or synthetic biodegradable or biodispersible polymers such as carbohydrates, including starches, gums and etherified or esterified cellulosic derivatives, polyethers, polyesters (particularly polylactide, polygylcolide or polylactide-glycolides), polyvinyl alcohols, gelatins, or alginates. Such dosage formulations can be prepared, for example, in the form of microsphere suspensions, gels (of hydrophilic or hydrophobic constitution), or shaped-polymer matrix implants that are well-known in the art for their function as "depot-type" drug delivery systems that provide prolonged release of the biologically active components. Such compositions can be prepared using art-recognized formulation techniques and designed for any of a wide variety of drug release profiles.

The administration of pharmaceutical compositions for use in the present invention can be intermittent or at a gradual, or continuous, constant, or controlled rate to a patient in need of treatment. In addition, the time of day and the number of times of day that the pharmaceutical formulation is administered can vary depending on the patient condition and environment. The level of efficacy and optimal dosage and dosage form for any given composition for use within the scope of this invention is patient-dependent and adjustable within reasonable ranges in the judgment of the attending physician. The formulation is typically administered over a period of time sufficient to treat or prevent the patient disease state, e.g., to modify the behavioral or cognitive performance of the patient undergoing treatment. The formulations may be continued to be administered using the same or attenuated dosage protocol for prophylaxis of the targeted disease state.

The above-described embodiments of the present invention derive in part from the mechanism of action suggested from data gathered in animal behavioral cognitive and skill models described below. Other embodiments of the invention will be apparent from analysis of the data obtained in the following non-limiting experimental examples, which are but illustrative of the behavior modification and cognitive performance and improvement attainable by use of the method and formulations of the present invention.

EXAMPLES

Example I

Synthesis of $\Delta_2$- and $\Delta^3$-Cefazolin Sulfoxides, Sodium Salts

Cefazolin. A solution of cefazolin, sodium salt, (998 mg, 2.095 mmol, commercial available from Chemifarma S. A., Madrid, Spain; Fujian Fukang Pharmaceutical Co., Ltd., Fuzhou, China) in water (100 mL) was treated with 1N aq. HCl (to pH 2.90). The resulting precipitate was suction-filtered and washed with water. The filtrate was made alkaline by treatment with 1N aq. NaOH (to pH 3.50), and then extracted with ethyl acetate (2×20 mL). The ethyl acetate extract was dried over $Na_2SO_4$, filtered, evaporated, and combined with the filtered material and dried to give 751 mg (79%) of the title compound.

$\Delta^2$- and $\Delta^3$-Cefazolin diphenylmethyl esters. To generate diphenyldiazomethane, $Pb(OAc)_4$ (986 mg, 2.22 mmol) was added to a stirred solution of benzophenone hydrazone (437 mg, 2.22 mmol) in dichloromethane (40 mL) containing tetramethylguanidine (3.84 g, 33.4 mmol) at −78° C. under $N_2$. After seventy min the reaction was quenched by the addition of cold (−20° C.) 30% aq. KOH (100 mL). The mixture was poured into a separatory funnel and treated with hexane (30 mL), shaken, and the layers separated. The organic layer was washed with more cold (−20° C.) 30% KOH (100 mL), and then the KOH washings were combined and back-extracted with hexane (20 mL). The hexane extracts were combined and washed with cold (−10° C.) 2% aq. KOH (5×150 mL), dried over $K_2CO_3$, and then used for the following reaction. For esterification, a mixture of cefazolin (674 mg, 1.48 mmol) and methylene chloride (250 mL) was treated with the entire hexane solution of diphenyldiazomethane at room temperature. After 1.5 hours, DMF (15 mL) was added, and the dichloromethane was slowly removed under reduced pressure at room temperature. Thirty minutes after the cefazolin had dissolved, acetic acid was added (2 mL). The DMF was removed under high vacuum, the residue was taken up in dichloromethane (5 mL), and added to a vigorously stirred solution of petroleum ether:hexane (1:1, 100 mL). The resulting gum was isolated, washed with petroleum ether, dissolved in dichloromethane (30 mL), and washed with saturated aq. $NaHCO_3$ (10 mL), dried over $Na_2SO_4$, filtered, and evaporated to give 875 mg (95%) of the title compounds in a 1:1.7 ratio, respectively.

$\Delta^2$- and $\Delta^3$-Cefazolin sulfoxide diphenylmethyl esters. A solution of the $\Delta^2$- and $\Delta^3$-cefazolin diphenylmethyl esters (875 mg, 1.41 mmol) in dichloromethane (20 mL) was treated with 30% $H_2O_2$ (196 mg, 1.83 mmol) and acetic acid (339 mg, 5.64 mmol). The resulting biphasic mixture was stirred for 18 hours and then worked up. The mixture was partitioned between dichloromethane (20 mL) and 20% aqueous $K_2CO_3$ (30 mL). The organic extract was dried over $Na_2SO_4$, filtered, evaporated, and the resulting oil was purified by column chromatography, $SiO_2$, Merck 70-230 mesh, 12 cm×5 cm, gradient mobile phase 50: 1-40:1-30: 1-25:1 $CH_2Cl_2$:MeOH to elute a first product and then 20: 1-10:1-15: 1-8:1 $CH_2Cl_2$:MeOH to elute a second product: 284 mg (32%) of the $\Delta^2$-isomer and 511 mg (57%) of the $\Delta^3$-isomer, respectively. $\Delta^2$-isomer: $^1$H-NMR ($CDCl_3$, 300 MHz) δ 8.92 (s, 1H), 8.33 (d, J=8.5 Hz, 1H), 7.50-7.21 (m, 10H), 6.89 (s, 1H), 6.29 (s, 1H), 5.57 (dd, J=8.5, 4.0 Hz, 1H), 5.47-5.29 (m, 3H), 4.25 (d, J=4.0 Hz, 1H), 3.93 (ABq, J=14.3 Hz, 2H), 2.67 (s, 3H). $\Delta^3$-isomer: $^1$H-NMR ($CDCl_3$, 300 MHz) δ 8.84 (s, 1H), 7.63 (d, J=9.6 Hz, 1H), 7.40-7.25 (m, 8H), 7.13-7.02 (m, 1H), 6.93 (s, 1H), 5.94 (dd, J=9.6, 4.4 Hz, 1H), 5.01 (ABq, J=17.5 Hz, 2H), 4.50 (d, J=4.4 Hz, 1H), 4.33 (ABq, J=13.7 Hz, 2H), 3.77 (ABq, J=18.8 Hz, 2H), 2.58 (s, 3H).

$\Delta^3$-Cefazolin sulfoxide. A solution of the $\Delta^3$-sulfoxide diphenylmethyl ester (505 mg, 793 μmol) and anisole (52 mg, 480 μmol) in dichloromethane (0.5 mL) was treated with trifluoroacetic acid (13 mL) at 0° C. for 90 min. The solvents were removed under reduced pressure, and the resulting oil was dissolved in dichloromethane (1 mL). Precipitation began to occur. Methanol was added, and the resulting white precipitate was collected by suction filtration to give 299 mg (80%) of the title compound. $^1$H-NMR (DMSO-$d_6$, 300 MHz) δ 13.90 (bs, 1H), 9.37 (s, 1H), 8.99 (d, J=8.5 Hz, 1H), 5.85 (dd, J=8.5, 4.3 Hz, 1H), 5.44 (ABq, J=17.2 Hz, 2H), 4.90 (d, J=4.3 Hz, 1H), 4.44 (ABq, J=13.7 Hz, 2H), 3.89 (ABq, J=18.3 Hz, 2H), 2.68 (s, 3H).

Δ2-Cefazolin sulfoxide. The Δ2-cefazolin sulfoxide was produced in an analogous manner starting from the $\Delta^2$-cefazolin sulfoxide diphenylmethyl ester (284 mg, 402 μmol), resulting in 190 mg (80%) of the title compound. $^1$H-NMR (DMSO-$d_6$, 300 MHz) δ 13.77 (bs, 1H), 9.57 (d, J=7.9 Hz, 1H), 9.36 (s, 1H), 6.71 (s, 1H), 5.51 (dd, J=7.9, 3.9 Hz, 1H), 5.36 (ABq, J=16.8 Hz, 2H), 5.18 (d, J=3.9 Hz, 1H), 5.08 (s, 1H), 4.21 (ABq, J=14.0 Hz, 2H), 2.70 (s, 3H).

$\Delta^3$-Cefazolin sulfoxide, sodium salt. A solution of $NaHCO_3$ (53 mg, 631 μmol) in water (6 mL) was added to a solution of the cefazolin sulfoxide (297 mg, 631 μmol) in DMSO (3 mL). The resulting solution was swirled, frozen and lyophilized to give an oil/solid mixture that was triturated with methanol/methylene chloride. The resulting solid was filtered with suction and washed with petroleum ether to give 283 mg (91%) of the title compound. $^1$H-NMR (DMSO-$d_6$, 300 MHz) δ 9.37 (s, 1H), 8.84 (d, J=8.2 Hz, 1H), 5.62 (dd, J=8.2, 4.4 Hz, 1H), 5.43 (ABq, J=16.9 Hz, 2H), 4.73 (d, J=4.4 Hz, 1H), 4.28 (ABq, J=12.6 Hz, 2H), 3.59 (ABq, J=18.1 Hz, 2H), 2.65 (s, 3H).

$\Delta^2$-Cefazolin sulfoxide, sodium salt. The $\Delta^2$-cefazolin sulfoxide sodium salt was produced in an analogous manner starting from the $\Delta^2$-cefazolin sulfoxide (189 mg, 402 µmol) resulting in 160 mg (81%) of the title compound. $^1$H-NMR (DMSO-$d_6$, 300 MHz) δ 9.56-9.46 (m, 1H), 9.36 (s, 1H), 6.31 (s, 1H), 5.50-5.10 (m, 5H), 4.35 (ABq, J=13.5 Hz, 2H), 2.69 (s, 3H).

Example II

Anxiety Behavioral Study

Dose-response in the Seed Finding Model of Anxiety

Rationale. The golden hamster seed finding model of anxiety is a robust and simple bioassay for screening beta-lactams for CNS activity. Briefly, hamsters are deprived of food overnight. The following day they are exposed to the additional stress of being taken from their home cage and placed in a novel environment for a few minutes. During their absence from the home cage, sunflower seeds are hidden under the bedding in one of the corners. When returned to the home cage, hamsters routinely scramble along the walls for 1-2 minutes before settling down, locating and eating the seeds. However, animals treated with the traditional anxiolytics, e.g., chlordiazepoxide, fluoxetine, or buspirone find seeds in less than 20 seconds (King J A, et al. (2001) *Neuropsychobiology* 45: 150-155). This reduction in seed finding time from minutes to seconds also occurs following treatment with certain beta-lactam antibiotics.

Experimental Protocol. Male golden hamsters were housed individually in Plexiglas cages (24 cm×24 cm×20 cm), maintained on a reverse light: dark cycle (14:10; lights on at 19:00 hr) and provided food and water ad libitum. Cefazolin-1-sulfoxide ($\Delta^3$-cefazolin sulfoxide) and delta-2-cefazolin-1-sulfoxide ($\Delta^2$-cefazolin sulfoxide) were each tested using four groups of four animals each over a range of doses (100 ng/kg, 10 µg/kg, 1 mg/kg, and saline vehicle as control) (FIGS. 1a-b). All tests were conducted during the dark phase of the circadian cycle under dim red illumination. Prior to testing all animals were fasted for 20-24 hours. Ninety minutes after oral gavage of drug, animals were taken from their home cage and placed into a holding cage for 2 minutes. During their absence, six sunflower seeds were buried under the bedding in one corner of their home cage. Animals were placed back into their home cage randomly facing any one of the empty corners and timed for their latency to find the seeds in a five minute observation period. Latency times were analyzed with a two-way ANOVA followed by Bonferroni's post hoc test.

Results. As illustrated in FIGS. 1a-b, both drugs, in doses of 100 ng/kg to 1 mg/kg, significantly (p<0.01) reduced latency to find the seeds as compared to saline vehicle with a mean latency of close to five minutes.

Summary. The data show cefazolins given orally to hamsters are effective in the seed finding test for anxiety. The seed finding assay appears to be a highly sensitive animal model for rapidly screening drugs for anxiolytic activity (King J A, et al. (2001) *Neuropsychobiology* 45: 150-155). The model appears to have empirical validity (McKinney, W. T. (1989) *Basis of development of animal models in psychiatry: An overview*. In: ANIMAL MODELS OF DEPRESSION, Eds. G. G. Koob, C. L. Ehlers, E. J. Kupfer Birkanser, Boston) i.e., anxiolytics like chlordiazepoxide, fluoxetine, and buspirone dramatically reduce seed finding at doses of 1 µg/kg and above, while drugs such as desipramine, yohimbine, and clozapine are ineffective.

Example III

Anxiety Behavioral Study

Anxiolytic Activity in the Elevated Plus-Maze

The elevated plus-maze was developed for the assessment of anxiolytic and anxiogenic drug effects in the rat (Pellow et al., (1985) *Journal of Neuroscience Methods* 14: 149-167). The method has been validated behaviorally, physiologically, and pharmacologically. The plus-maze has two open arms and two enclosed arms. Rats will naturally make fewer entries into the open arms (light) than into the closed arms (dark) and will spend significantly less time in open arms. Confinement to the open arms is associated with significantly more anxiety-related behavior and higher stress hormone levels than confinement to the closed arms. Clinically effective anxiolytics, e.g., chlordiazepoxide or diazepam, significantly increase the percentage of time spent in the open arms and the number of entries into the open arms. Conversely, anxiogenic compounds such as yohimbin or amphetamines reduce open arm entries and time spent in the open arms.

Method. Male Wistar rats weighing 250-300 g were group housed in a normal 12:12 light-dark cycle light on at 0800 hour and provided food and water ad libitum. The plus-maze consisted of two open arms, 50×10 cm, and two enclosed arms 50×10×40 cm with an open roof, arranged such that the two open arms were opposite to each other. The maze was elevated to a height of 50 cm. Four groups of five animals each were tested in the plus-maze 90 minutes following oral gavage of either vehicle, or 100 ng/kg, 10 µg/kg, or 1 mg/kg of delta-2-cefazolin-1-sulfoxide ($\Delta^2$-cefazolin sulfoxide). At the start of the experiment the animal was place in the center of the plus maze facing the closed arm. Over a 3 minute observation period, animals were scored for the latency to enter the closed arm, time spent in the closed arm, and the number of open arm entries following the first occupation of the closed arm.

Figures 2A, 2B:
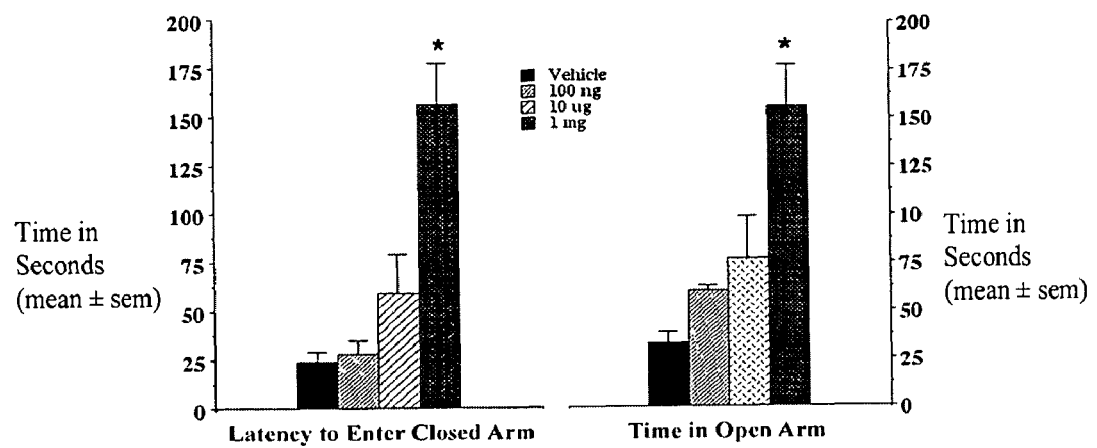
FIGS. 2*a-b* show results using $\Delta^2$-cefazolin-1-sulfoxide in an elevated plus-maze study.
Figures 3A, 3B:
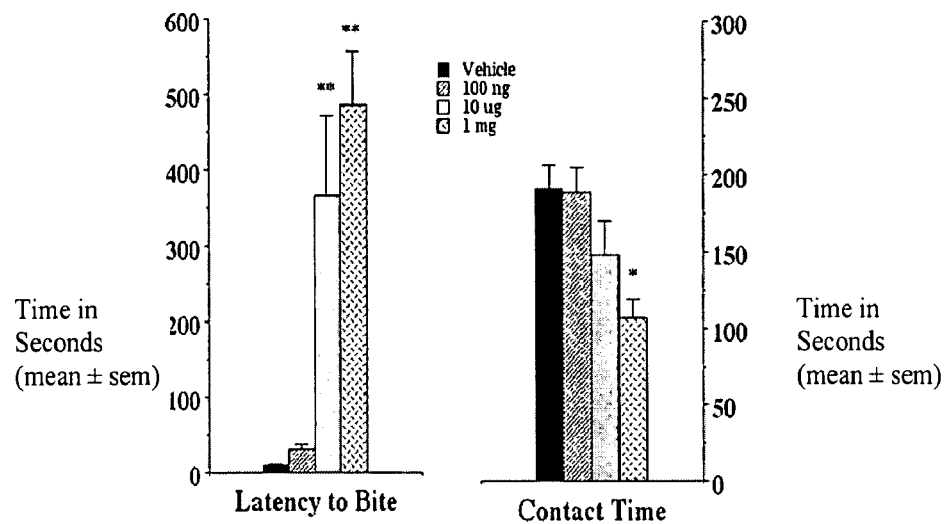
FIGS. 3*a-d* show results of testing for serenic activity in a resident/intruder model system using $\Delta^2$-cefazolin-1-sulfoxide.
Figures 3C, 3D:
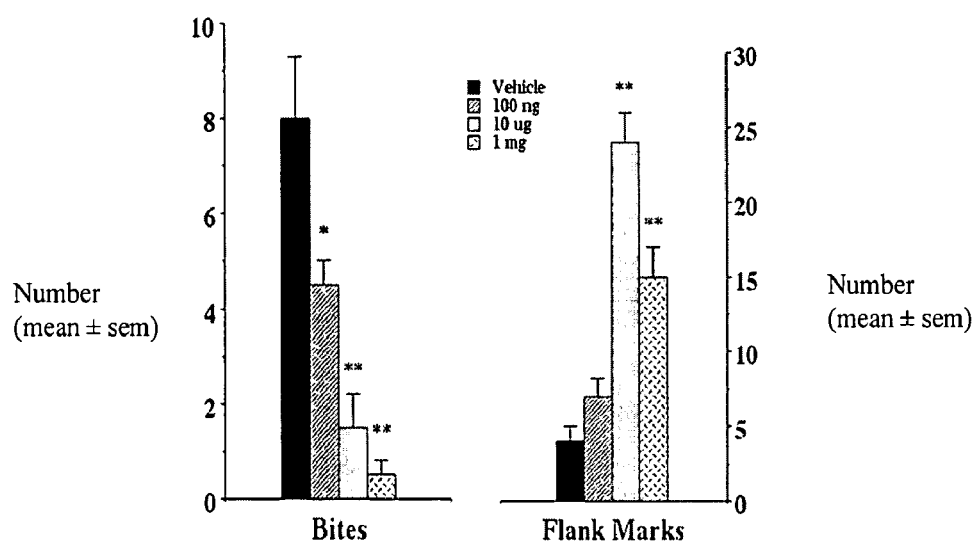

Results. Treatment with delta-2-cefazolin-1-sulfoxide ($\Delta^2$-cefazolin sulfoxide) increased the latency to enter the closed arm (p<0.05) as compared to vehicle (FIG. 2a), while the time spent in the open was significantly increased (p<0.01) as compared to vehicle (FIG. 2b).

Summary. $\Delta^2$-cefazolin sulfoxide given orally to rats shows dose-dependent anxiolytic activity in the elevated plus-maze.

Example IV

Testing for Serenic Activity

Agonistic behavior can be classified as either offensive or defensive aggression (Blanchard, R. J., Blanchard, D. C. (1977) *Physiology and Behavior*, 1, 197-224; Adams, D. B. (1979) *The Behavioral Brain Sciences*, 2, 201-241; Albert, D. J. and Walsh, M. L. (1984) *Neuroscience and Behavioral Reviews*, 8, 5-24). Offensive aggression is characterized by the aggressor initiating an attack on an opponent, while defensive aggression lacks active approach. Both types of aggression have their own unique neurobehavioral systems.

The stimuli that elicit offensive and defense attacks are different, as are the sequences of behaviors that accompany each agonistic response. While much of the empirical data supporting the notion of unique offensive and defensive neural networks have been collected from animal models, there are interesting and compelling similarities in human aggression that suggest a similar neural organization (Blanchard, D. C. (1984) *Applicability of animal models to human aggression* In: BIOLOGICAL PERSPECTIVES ON AGGRESSION, Alan R. Liss, Inc. pgs 49-74). Offensive aggression is easily studied using male golden hamsters tested in a resident/intruder paradigm, an established model of offensive aggression (Ferris, C. F., Potegal, M. (1988) *Physiology and Behavior*, 44, 235-239). Placing an unfamiliar male hamster into the home cage of another male hamster elicits a well-defined sequence of agonistic behaviors from the resident that includes offensive aggression.

Animal Care. Male Syrian golden hamsters (*Mesocricetus auratus*) (140-150 g) obtained from Harlan Sprague-Dawley Laboratories (Indianapolis, Ind.) were housed individually in Plexiglas cages (24 cm×24 cm×20 cm), maintained on a reverse light:dark cycle (14L:10D; lights on at 19:00 hr) and provided food and water ad libitum. Animals were acclimated to the reverse light:dark cycle for at least two weeks before testing. All behavioral tests were conducted during the dark phase of the circadian cycle.

Behavioral Measures and Analysis. Hamsters are nocturnal and as such behavioral tests were performed during the first four hours of the dark phase under dim red illumination. The resident was scored for offensive aggression, e.g., latency to bite the intruder, total contact time with the intruder, the total number of bites, and flank marking, over a 10 minute test period (Ferris, C. F., Potegal, M. (1988) *Physiology and Behavior*, 44, 235-239). Flank marking is a form of olfactory communication in which a hamster arches its back and rubs pheromone producing flank glands against objects in the environment (Johnston, R. E. (1985) Communication, In: THE HAMSTER REPRODUCTION AND BEHAVIOR. Ed Siegel, H. I. Plenum Press, New York, pp 121-154). Flank marking frequency is greatly enhanced during aggressive encounters and is particularly robust in dominant animals initiating and winning fights (Ferris, C. F., et al., (1987) *Physiology and Behavior*, 40, 661-664).

Parametric data, i.e., latencies and contact time, were analyzed with a one-way ANOVA followed by Newman-Keuls post hoc tests. Non-parametric data, i.e., number of bites and flank marks, were analyzed with Kruskal-Wallis tests followed by Mann-Whitney U tests to determine differences between groups.

Figure 4A:
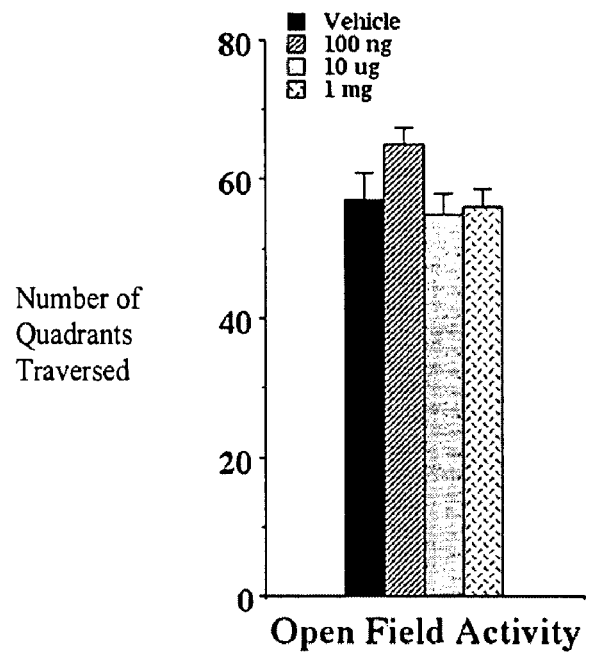
FIGS. 4*a-b* show motor activity subsequent to the resident/intruder test summarized in FIGS. 3*a-d*, with FIG. 4*a* showing open field activity and FIG. 4*b* showing sexual motivation.
Figure 4B:
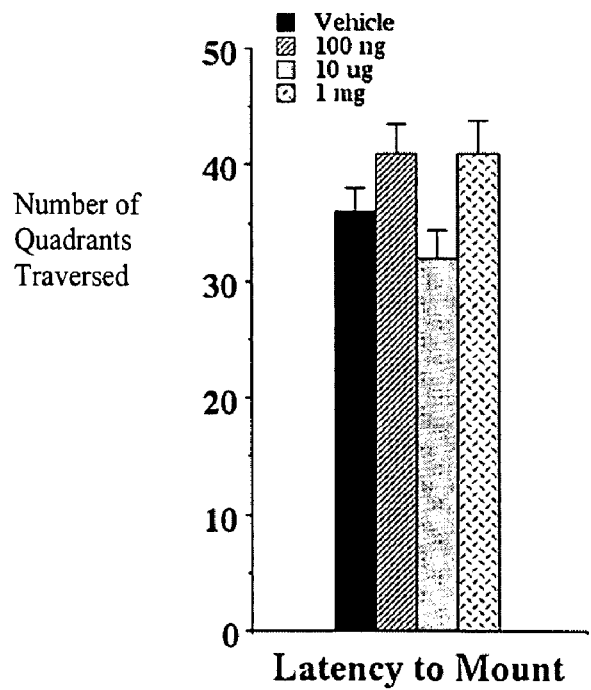

Method. Delta-2-cefazolin-1-sulfoxide ($\Delta^2$-cefazolin sulfoxide) was tested using four groups of five animals each over a range of doses (100 ng/kg, 10 µg/kg, 1 mg/kg, and saline vehicle as control) (FIGS. 3a-d). Ninety min after oral gavage an intruder was placed into the home cage and the resident scored for offensive aggression. Following aggression testing, animals were screened for motor activity in an open field paradigm and sexual motivation (FIGS. 4a-b).

Results. The latency to bite was significantly increased and the number of bites decreased by delta-2-cefazolin-1-sulfoxide ($\Delta^2$-cefazolin sulfoxide) treatment (p<0.01). While contact time was significantly reduced at the highest dose, flank marking was significantly increased.

Summary. These data show delta-2-cefazolin-1-sulfoxide ($\Delta^2$-cefazolin sulfoxide) to be a very effective serenic, inhibiting offensive aggression. Flank marking, an olfactory driven behavior, is not reduced. As shown in FIGS. 4a-b, there is no change in motor activity or sexual motivation, demonstrating that the reduction in aggression is not due to decreased activity or appetitive behavior.

Example V

Testing for Learning and Memory in the Radial Arm Maze

The radial arm maze is one of the most commonly used methods for testing spatial learning and memory in rodents. Developed by Olton and co-workers (Olton, D. S., Samuelson, R. J. (1976) *J. Experimental Psychology*, 2: 97-115), the maze provides the simultaneous choice of several alternative paths for the test subject. Animals must learn which locations provide food (place learning) using visuospatial cues.

Animal care. Male BALBc mice weighing 21-23 gm were housed individually in a normal 12:12 light-dark cycle (light on at 0600 hr) and provide food and water ad libitum. The method described below was reported by Crusio et al., (1987) *Brain Research*, 425: 182-185. The radial arm maze consisted of a central platform and eight arms made of transparent Plexiglas. The central part measured 22 cm in diameter. The closed arms were 25 cm long, 6 cm high and 6 cm wide. Several fresh food pellets were deposited beyond the end of each arm behind a perforated wall. This arrangement served to prevent the animals from selecting a baited arm by smelling the presence or absence of a reward. All arms were baited by placing a food pellet (about 10 mg) behind a low barrier. The maze was placed on the floor and several extramaze cues were provided close to the maze and between the arms. At the start of each trial, the mouse was placed in the center of the maze and allowed free choice of all eight arms. Between choices, the mouse was confined in the center of the maze for 5 seconds by means of transparent guillotine doors at the entrance of each arm. Mice received a 10 minute habituation trial with free access to all arms 24 hours prior to training. Subsequently, the mice were deprived of food but not of water. During training, the body weight was kept at 85% of the pretest body weight.

Figure 5:
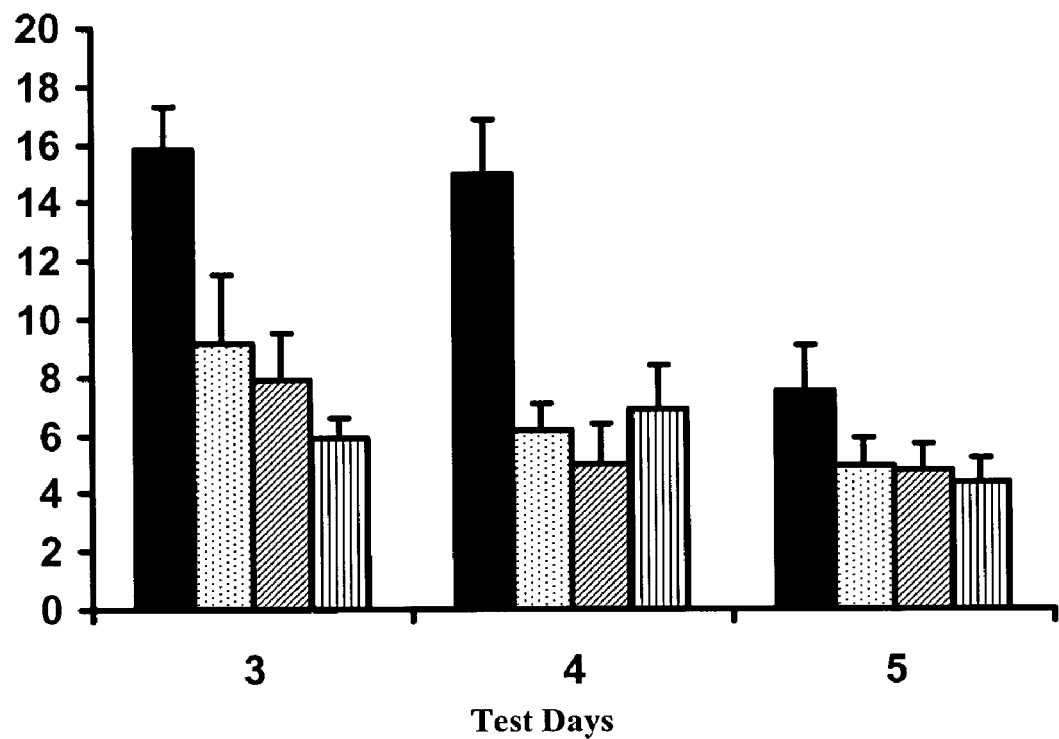
FIG. 5 shows the number of errors demonstrating learning and memory in a radial arm maze system.

Method. Cefazolin-1-sulfoxide ($\Delta^3$-cefazolin sulfoxide) was tested using four groups of six or seven animals each over a range of concentrations (saline vehicle, 2.5 ng, 250 ng, 25 µg/kg) (FIG. 5). Training took place, sixty to ninety minutes after intra-peritoneal injection of 0.05 ml. $\Delta^3$-cefazolin sulfoxide on five consecutive days with one trial per day. A trial was terminated when the animal had eaten all rewards or after 15 min. Entry to an arm was counted when the mouse reached the perforated wall. An error was noted if an animal entered an arm previously visited. The number of errors was recorded for each day of training. Only data from the last three days of training were used for subsequent analysis. Dose response effects were assessed by means of a repeated measured two-way ANOVA followed by Bonferroni's post hoc test.

Results. Treatment with $\Delta^3$-cefazolin sulfoxide significantly reduced (*p<0.05, **p<0.01) the number of errors on testing days three and four as compared to vehicle control (FIG. 5). By day five mice treated with vehicle showed a significant decrease in errors (p<0.05) as compared to days three and four. By day five there was no significant difference in errors between any of the treatment groups and vehicle.

Summary. In the radial arm maze, intra-peritoneal administration of $\Delta^3$-cefazolin sulfoxide reduced the numbers of incorrect arm entries as compared to vehicle control suggesting enhancement of spatial memory in this cognitive test. The performance of mice treated with vehicle increased over time so that by the end of the five day testing period their performance essentially matched that of the cefazolin treated animals.

Example VI

Microdialysis Studies

The biological profile of cefazolin-1-sulfoxide ($\Delta^3$-cefazolin sulfoxide) e.g., anti-anxiety, reduced aggression and enhanced learning, suggests a mechanism of action that would involve serotonergic and catecholaminergic neurotramsmission. To test this hypothesis, extracellular neurotransmitter levels in the area of the nucleus accumbens were assessed with microdialysis following $\Delta^3$-cefazolin sulfoxide treatment. The accumbens is part of the limbic forebrain best know for its association with the pathophysiology of schizophrenia, conditioned reinforcement and drug addiction but also thought to be involved in sensitization to early life trauma leading to the anxiety disorder PTSD or post traumatic stress disorder (Charney and Bremner (1999) *The neurobiology of anxiety disorder*. In: NEUROBIOLOGY OF MENTAL ILLNESS (Cahrney, D S, et al eds.), Oxford University Press, New York, pgs 494-517).

Figure 6A:
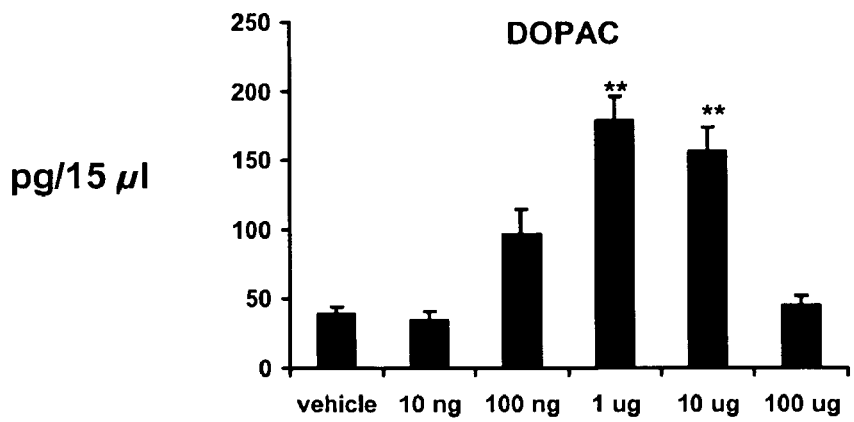
FIGS. 6*a-c* show levels of dopamine metabolites DOPAC (FIG. 6*a*) and HVA (FIG. 6*b*) and serotonin metabolite (FIG. 6*c*), all pg/15 µl, subsequent to treatment with $\Delta^3$-cefazolin-1-sulfoxide, as assessed by electrochemical detection.
Figure 6B:
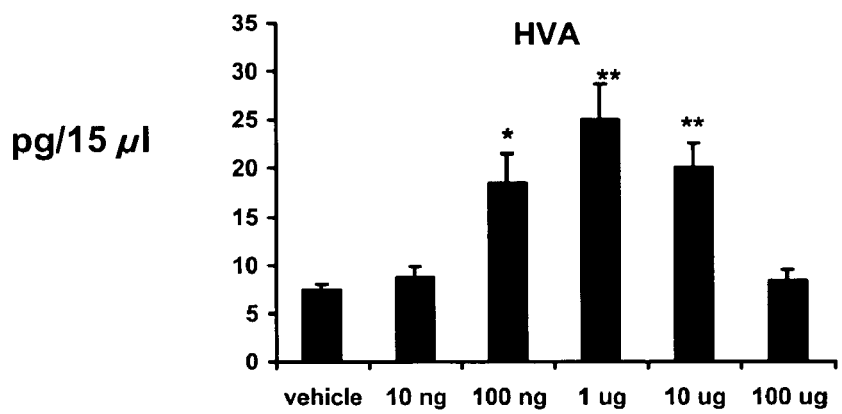
Figure 6C:
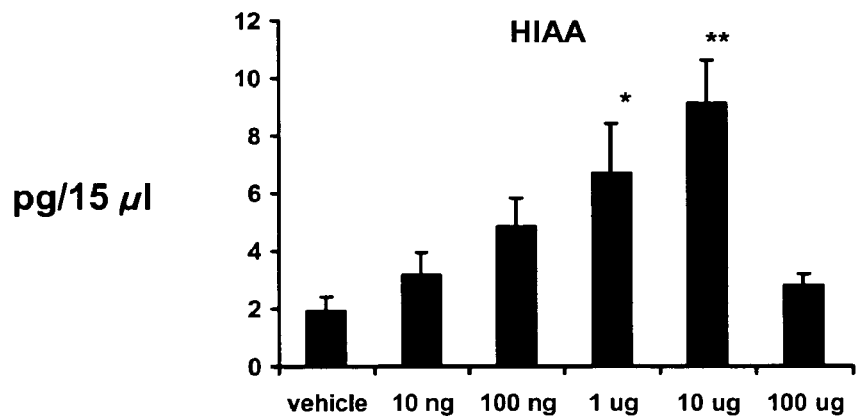

Method. Twenty-four male Sprague Dawley rats were anesthetized with sodium pentobarbital (50 mg/kg) and implanted with a unilateral microdialysis guide cannula aimed at the nucleus accumbens. Animals were divided into six groups of four animals each and treated with a range of cefazolin doses (saline vehicle, 10 ng, 100 ng, 1 µg, 10 µg, 100 µg/kg) (FIGS. 6a-c). Two days after recovery from surgery a microdialysis probe (2 mm) was lowered to the area and connected to an infusion pump through Tygon tubing. The dialysate was artificial CSF at pH 7.4 delivered at a flow rate of 1.8 µl/min. The first 30 minutes of dialysate was discarded. Thereafter, samples were collected at 15 minute intervals 45 minutes prior to and 75 minutes following intra-peritoneal administration of $\Delta^3$-cefazolin sulfoxide. Samples were collected into microfuge tubes containing 5 µl of 0.16 N perchloric acid to stabilize catecholamines. At the end of the study, animals were sacrificed and the brains prepared for histology to verify the site of the microdialysis probe.

The levels of dopamine metabolites DOPAC (FIG. 6a) and HVA (FIG. 6b) and serotonin metabolite HIAA (FIG. 6c) were assessed by electrochemical detection. The first 15 minute sample after intra-peritoneal injection was excluded from the analysis because of variability caused by handling the animal for drug administration. Measures from each of the four remaining samples collected between 15-75 minutes post-treatment were analyzed. Samples from each animal, in each group, for each metabolite (total of 16 samples) were averaged. Mean values were analyzed with a one-way ANOVA followed by Bonferroni's post hoc test.

Results. There was a significant (*$p<0.05$; **$p<0.01$) dose-dependent increase in DOPAC, HVA, and HIAA levels following $\Delta^3$-cefazolin sulfoxide treatment.

Summary. These microdialysis studies indicate $\Delta^3$-cefazolin sulfoxide increases serotonin and dopamine neurotransmission in the nucleus accumbens. Recent advances in the treatment of anxiety disorders, impulsivity and violence have focused on the activation of the serotonin neurotransmission (Feighner J P. (1999) *J. Clinical Psychiatry*. 60: 18-22; Ferris, C. F. et al. (1997) *J. Neuroscience*, 17: 4331-4340; Coccaro et al. (1998) *Archives of General Psychiatry*, 55: 708-714.). Given the work in this area it is not surprising that $\Delta^3$-cefazolin sulfoxide's release of serotonin is accompanied by robust anti-anxiety and serenic behavior in animal models.

The activation of serotonin and dopamine neurotransmission in the nucleus accumbens raises the possibility that cefazolin sulfoxide be used to treat drug addiction, obesity, and schizophrenia. Work by scientists at the National Institute of Drug Abuse and the National Institute of Diabetes and Digestive and Kidney Diseases have shown that the combined administration of amphetamine analogs phentermine and fenfluramine (PHEN/FEN) increases extracellular dopamine and serotonin levels in the nucleus accumbens of rats (Baumann et al., (2000) *Synapse*, 36: 102-113). PHEN/FEN is an effective pharmacotherapy for obesity (Weintraub et al., (1984) *Archive of Internal Medicine*, 144: 1143-1148) and in open clinical trials decreased cocaine craving, alleviated withdrawal symptoms and prolonged drug abstinence (Rothman et al. (1994) *J. Substance Abuse Treatment*, 11: 273-275). Scientists at the National Institutes of Health concluded drugs with a similar mechanism to PHEN/FEN causing increased neurotransmission of serotonin and dopamine in the nucleus accumbens may have utility in the treatment of substance abuse and obesity.

Work by scientists from Eli Lilly and Company (Indianapolis, Ind.) used microdialysis and ex vivo tissue analysis of prefrontal cortex and nucleus accumbens to evaluate the mechanism of action of a metabotropic glutamate receptor agonists being developed for the treatment of psychosis (Cartmell et al., (2000) *Brain Research*, 887: 378-384; Cartmell et al. (2000) *J. Neurochemistry* 75: 1147-1154). Atypical antipsychotics such as risperidone increase dopamine and serotonin neurotransmission in the prefrontal cortex and nucleus accumbens (Cartmell et al. (2000) *J. Neurochemistry*, 75: 1147-1154; Hertel et al. (1996) *Psychopharmacology*, 124: 74-86). The Lilly scientists found that activation of metabotropic glutamate receptors has a similar mechanism elevating DOPAC, HIAA and HVA in these brain areas.

Example VII

Each of $\Delta^2$-cefazolin sulfoxide and $\Delta^3$-cefazolin sulfoxide, or a combination thereof, is combined with a pharmaceutically acceptable tableting mixture to provide respective tableting compositions which are compressed into tablets or filled into gelatin capsules containing 100 ng, 1 µg, 10 µg, 100 µg, 1 mg, 10 mg, 50 mg, 100 mg, 200 mg, 350 mg, and 500 mg of $\Delta^2$- or $\Delta^3$-cefazolin sulfoxide, or a combination thereof, per tablet/capsule.

Example VIII

A patient suffering from ADHD is administered a formulation from EXAMPLE VII above to ameliorate symptoms of the disease.

Example IX

A patient suffering from a neurological disorder characterized by aggressive behavior is treated two to three times a day with a formulation of Example VII above to reduce patient aggressive behavior.

Example X

A patient suffering from dementia is treated three times a day with a formulation of Example VII above to produce improved patient cognition.

Example XI

A patient suffering from an anxiety disorder is administered a formulation of Example VII above two to three times a day to reduce patient anxiety.

Although the invention has been described in detail with reference to certain preferred embodiments, variations and modifications exist within the scope and spirit of the invention as described and defined in the following claims.

The invention claimed is:

1. A neurotherapeutic pharmaceutical formulation in oral dosage form, said formulation comprising a neurotherapeutic compound in an effective amount for treating a neurological disease, a behavioral disorder, or a cognitive disorder; wherein the compound is selected from the group consisting of $\Delta^2$-cefazolin sulfoxide, $\Delta^3$-cefazolin sulfoxide, $\Delta^2$-cefazolin sulfone, $\Delta^3$-cefazolin sulfone, $\Delta^2$-ceftriaxone sulfoxide, $\Delta^3$-ceftriaxone sulfoxide, $\Delta^2$-ceftriaxone sulfone, $\Delta^3$-ceftriaxone sulfone, combinations thereof, pharmaceutically acceptable salts thereof, and active esters thereof.

2. The neurotherapeutic pharmaceutical formulation of claim 1 wherein the compound is selected from the group consisting of $\Delta^2$-cefazolin sulfoxide, $\Delta^3$-cefazolin sulfoxide, combinations thereof, pharmaceutically acceptable salts thereof, and active esters thereof.

3. A compound of the formula:

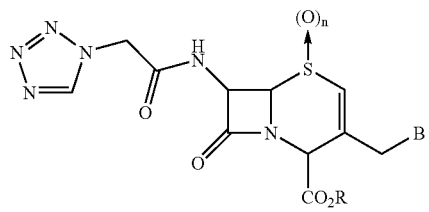

wherein n is 1 or 2; R is hydrogen, an active ester forming group, or a pharmaceutically acceptable cation; and B is

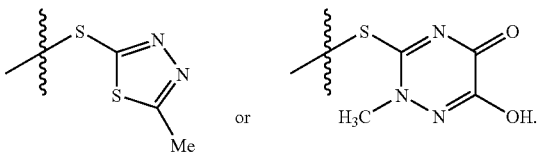

4. The compound of claim 3 wherein R is selected from the group consisting of indanyl, acyloxyalkyl, and alkyloxycarbonyloxyalkyl.

5. The compound of claim 3 wherein R is selected from the group consisting of 1-indanyl, acetoxyalk-1-yl, isopropoxycarbonyloxyalk-1-yl, and pivaloyloxyalk-1-yl.

6. A compound of the formula:

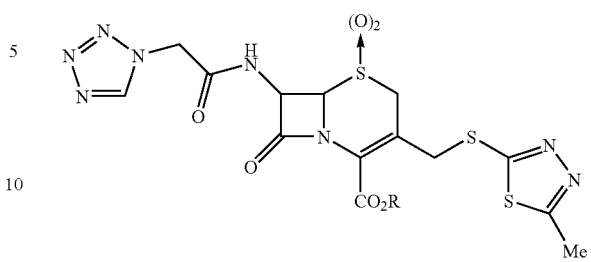

wherein R is hydrogen, an active ester forming group, or a pharmaceutically acceptable cation.

7. The compound of claim 6 wherein R is selected from the group consisting of indanyl, acyloxyalkyl, and alkyloxycarbonyloxyalkyl.

8. The compound of claim 6 wherein R is selected from the group consisting of 1-indanyl, acetoxyalk-1-yl, isopropoxycarbonyloxyalk-1-yl, and pivaloyloxyalk-1-yl.

9. A compound of the formula:

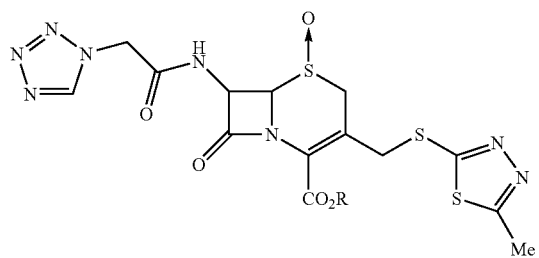

wherein R is selected from the group consisting of indanyl, acyloxyalkyl, and alkyloxycarbonyloxyalkyl.

10. A compound of the formula:

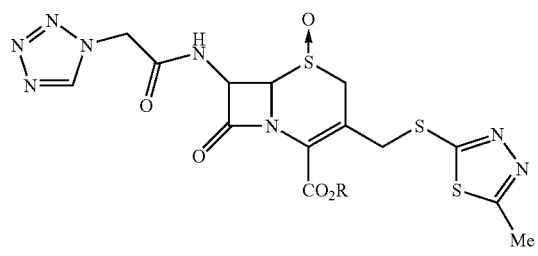

wherein R is selected from the group consisting of 1-indanyl, acetoxyalk-1-yl, isopropoxycarbonyloxyalk-1-yl, and pivaloyloxyalk-1-yl.

* * * * *